US006225437B1

(12) United States Patent
Hu et al.

(10) Patent No.: US 6,225,437 B1
(45) Date of Patent: May 1, 2001

(54) SIZING AGENTS OF ENHANCED PERFORMANCE CAPABILITIES

(75) Inventors: Patrick C. Hu; Valerie N. LeGloahec, both of Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/339,669

(22) Filed: Jun. 24, 1999

(51) Int. Cl.$^7$ .......................... C08G 69/08; C08G 73/00; D21H 17/05

(52) U.S. Cl. ........................ 528/328; 528/342; 528/345; 528/363; 525/418; 525/419; 525/420; 525/422; 524/600; 524/602; 162/158; 162/164.1; 162/164.6; 162/168.1; 162/168.2; 162/175; 162/180; 162/181.8; 162/184; 162/185; 162/202; 162/205

(58) Field of Search .................................. 528/328, 342, 528/345, 363; 525/420, 418, 419, 422; 162/158, 164.1, 168.1, 168.2, 164.6, 175, 180, 181.8, 184, 185, 202, 205; 524/600, 602

(56) References Cited

U.S. PATENT DOCUMENTS

| | | | |
|---|---|---|---|
| 3,087,936 | 4/1963 | LeSuer | 260/326.3 |
| 3,102,064 | 8/1963 | Wurzburg et al. | 162/158 |
| 3,324,033 | 6/1967 | Knapp | 252/51.5 |
| 3,391,175 | 7/1968 | Davis | 260/448 |
| 3,391,219 | 7/1968 | Davis et al. | 260/683.15 |
| 3,476,774 | 11/1969 | Zaweski et al. | 260/346.8 |
| 3,623,985 * | 11/1971 | Hendrickson | 252/51.5 A |
| 3,725,434 | 4/1973 | Elliott et al. | 260/326.3 |
| 3,726,822 | 4/1973 | von Bonin et al. | 260/29.6 RW |
| 3,821,069 | 6/1974 | Wurzburg | 162/158 |
| 3,855,251 | 12/1974 | Cahill | 260/346.8 R |
| 3,912,764 | 10/1975 | Palmer, Jr. | 260/346.8 |
| 3,927,041 | 12/1975 | Cengel et al. | 260/346.8 |
| 3,993,640 | 11/1976 | Pickard et al. | 536/30 |
| 4,086,251 | 4/1978 | Cengel et al. | 260/346.74 |
| 4,234,435 | 11/1980 | Meinhardt et al. | 252/51.5 A |
| 4,431,826 | 2/1984 | Sweeney | 549/255 |
| 4,576,680 | 3/1986 | Kawatani et al. | 162/158 |
| 4,839,415 | 6/1989 | Schurmann et al. | 524/549 |
| 4,883,886 | 11/1989 | Huang | 549/255 |
| 4,958,034 | 9/1990 | Hale et al. | 549/255 |
| 5,021,169 | 6/1991 | Shin et al. | 549/255 |
| 5,104,486 | 4/1992 | Sweeney | 162/158 |
| 5,114,538 | 5/1992 | Malatesta | 162/158 |
| 5,246,491 | 9/1993 | Takahashi et al. | 106/287.24 |
| 5,286,799 * | 2/1994 | Harrison et al. | 525/285 |
| 5,319,030 * | 6/1994 | Harrison et al. | 525/285 |
| 6,015,776 * | 1/2000 | Harrison et al. | 508/192 |

FOREIGN PATENT DOCUMENTS

| | | |
|---|---|---|
| 0122617 | 10/1984 | (EP) . |
| 0169250 | 1/1986 | (EP) . |
| 1422302 | 1/1976 | (GB) . |
| 1588416 | 4/1981 | (GB) . |
| 2082067 | 3/1982 | (GB) . |
| 9611193 | 4/1996 | (WO) . |

OTHER PUBLICATIONS

Fleckner, et al., "Tricarbonylbis(n2–cis–cyclooctene)iron: Photochemical Synthesis of a Versatile Fe(CO)$^3$ Source for Olefin Isomerization and Preparative Applications", J. Am. Chem. Soc., 1984, vol. 106, pp. 2027–2032, The month in the date of publication is not available.

Kane, et al., "Catalytic Isomerisation of Alkenes by Fe(CO)$^{4-}$", Polyhedron, vol. 4, No. 4, 1985, pp. 533–538, The month in the date of publication is not available.

Darsillo, et al., "Photoassisted Catalysis of the 1–Pentene Isomerization by Fe(CO)$^5$ Physisorbed onto Porous Vycor Glass", Inorg. Chem., 1988, vol. 27, pp. 2815–2819, The month in the date of publication is not available.

Caplus Abstract of JP 57154495 dated 1982, Sep. 24.

WPIDS Abstract of JP 57154495 dated 1982, Sep. 24.

Kirk–Othmer, Encyclopedia of Chemical Technology, 3rd Edition, vol. 16, John Wiley & Sons, 1981, pp. 803–825.

Encyclopedia of Polymer Science and Technology, Plastics, Resins, Rubbers, Fibers, vol. 9, John Wiley & Sons, Inc., 1968, pp. 748–793.

XP –002144388 –Derwent Absract of JP 5039390, issued 1993.

XP –002144389 –Derwent Abstract of JP 54028389, issued 1979.

* cited by examiner

Primary Examiner—P. Hampton-Hightower
(74) Attorney, Agent, or Firm—Philip M. Pippenger

(57) ABSTRACT

Provided are alkenyl and/or alkyl succinimides formed from at least one alkenyl or alkyl succinic anhydride and at least one aliphatic amine having one or two primary amino groups in the molecule. These succinimides are characterized in that each alkenyl or alkyl group thereof contains in the range of 16 to 30 carbon atoms. Such group is bifurcated on its alpha carbon atom into two branches neither of which contains less than 2 carbon atoms, one such branch being free of any side chain, and the other such branch either being free of any side chain or containing at most one methyl or methylene side chain. In addition the succinimide has a viscosity at 80° C. of less than about 100 centistokes. These succinimides are especially useful as internal and external sizing agents for paper and paper products.

26 Claims, No Drawings

SIZING AGENTS OF ENHANCED PERFORMANCE CAPABILITIES

BACKGROUND

It has been proposed heretofore to use certain imide-containing compounds or certain imide-containing polymers as sizing agents for paper and similar products. However, two other types of sizing agents have achieved widespread commercial acceptance in the marketplace for this use. These are certain alkenyl ketene dimers, and certain alkenyl succinic anhydrides such as an alkenyl succinic anhydride in which the alkenyl group is derived from a mixture of internal olefins composed on a weight basis of approximately 4% $C_{14}$, 50% $C_{16}$, 45.5% $C_{18}$, and 0.5% $C_{20}$ olefins.

Among the excellent properties of the alkenyl succinic anhydride paper sizing agents such as that described above are that it has high reactivity toward cellulose, and that it imparts an antiskidding property to sized papers. Unfortunately the anhydride is reactive to water and this can detract somewhat from realization of the full potential of sizing effectiveness inherent in the product.

It would be of considerable benefit if new, non-polymeric sizing agents could be found that have higher hydrolytic stability than alkenyl succinic anhydride paper sizing agents, and that possess beneficial performance capabilities as paper sizing agents. In addition, it would be of advantage to find paper sizing agents that are equally efficacious when used either as internal sizing agents or external sizing agents.

This invention is deemed to fulfill the foregoing objectives.

SUMMARY OF THE INVENTION

Pursuant to this invention there are provided new sizing agents for cellulosic products with properties rendering them useful in the manufacture of a variety of products, such as paper, cardboard, wall board, gypsum board, and like materials. Moreover, other potential applications exist for various new compositions of this invention.

Thus, in accordance with one of its embodiments, this invention provides one or a mixture of alkenyl and/or alkyl succinimides formed from one or a mixture of alkenyl or alkyl succinic anhydrides and at least one aliphatic amine having one or two primary amino groups in the molecule, said alkenyl and/or alkyl succinimide being characterized in that:

a) each alkenyl or alkyl group of such succinimide contains in the range of about 12 to about 30 carbon atoms, and is bifurcated on its alpha carbon atom into two branches neither of which contains less than 2 carbon atoms, one such branch being free of any side chain, and the other such branch either being free of any side chain or containing at most one methyl or methylene side chain; and b) the succinimide has a viscosity at 80° C. of less than about 100 centistokes.

Preferred aliphatic amines used in forming the above succinimide(s) are alkyl or alkenyl primary monoamines, alpha omega alkylene diamines, alkylene polyamines having two terminal primary amino groups and at least one internal secondary amino group, and alkylene polyamines having one terminal primary amino group and at least one secondary or tertiary amino group.

The succinimides of this invention can be composed of one single compound meeting the above requirements, or they can be a mixture of two or more compounds meeting the above requirements. When the succinimides of this invention are in the form of a mixture, the mixture can differ in various respects. In one embodiment, the mixture can differ only in the chain lengths of the alkenyl and/or alkyl groups in the respective molecules. In another embodiment the mixture can be made from a mixture of two or more species of one type of amine (e.g., a mixture of, say, $C_{16}$ and $C_{18}$ alkyl or alkenyl monoamines, or a mixture of, say, ethylene diamine and hexamethylene diamine, or a mixture of, say, diethylene triamine, triethylene tetramine, and tetraethylene pentamine). In still another embodiment the mixture can be made from a mixture of at least two different types of amines (e.g., a mixture, say, of a monoamine and a polyamine, or a mixture of an alkylene polyamine and a polyalkylene polyamine).

In a preferred embodiment the succinimides of this invention comprise at least one alkenyl or alkyl succinimide in which (i) there are from 1 to 2 imidized alkenyl or alkyl succinic moieties per molecule, (ii) the alkenyl or alkyl group of each such moiety contains in the range of about 12 to about 30 carbon atoms, (iii) each such alkenyl or alkyl group is bifurcated on its alpha carbon atom into two branches neither of which contains less than 2 carbon atoms, one such branch being free of any side chain, and the other such branch either being free of any side chain or containing at most one methyl or methylene side chain, (iv) the imidizing moiety of the succinimide has one of the formulas (1) through (5) as follows:

  (1)

  (2)

  (3)

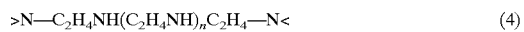  (4)

  (5)

where $R^1$ is (a) an alkyl group or (b) an olefinically unsaturated aliphatic hydrocarbon group having therein from 1 to 3 olefinic double bonds, said group (a) or (b) having in the range of 2 to about 20 (preferably 4 to about 18) carbon atoms, $R^2$ is a hydrogen atom or an alkyl group, n is an integer in the range of 0 to 5, and $R^2$ has a total number of carbon atoms in the range of 2 to about 15, and $R^3$ is an alkylene group having from 2 to about 10 carbon atoms, and (v) the succinimide has a viscosity at 80° C. of less than about 100 centistokes. Of these succinimides, those in which the imidizing moiety is of Formula (1) are preferred. Also preferred are those of which the imidizing moiety is of Formula (4).

In one preferred embodiment the succinimide(s) described above is one or a mixture of such compounds which is a solid at room temperature (e.g., in the range of about 20 to about 25° C.) and which has a melting temperature in the range of about 30 to about 100° C.

The succinimides of this invention can be formed by reaction of the appropriate internal olefin or mixture of appropriate internal olefins with maleic anhydride at a suitable temperature at which the so-called "ene" reaction occurs (e.g., 250° C.). The resultant alkenyl succinic anhydride is then reacted with a suitable amine or mixture of amines to produce the succinimide. Such a reaction is sometimes referred to as an "imidization reaction". To produce the corresponding alkyl succinimide(s), either the alkenyl succinic anhydride(s) or the alkenyl succinimide(s) is/are subjected to hydrogenation under a pressurized hydrogen atmosphere in the presence of a suitable catalyst such as palladium on charcoal.

The olefin(s) used to make the alkenyl succinic anhydride (s), and thus the alkenyl group(s) of both the alkenyl succinic anhydride(s) and the alkenyl succinimide(s), can have odd numbers of carbon atoms or even numbers of carbon atoms, or can be mixtures of odd and even numbers of carbon atoms. Alkenyl succinimides ultimately produced from olefin mixtures in which all olefin components, or substantially all olefin components (e.g., at least about 95 wt % of the olefins) are even numbered olefins, are preferred.

Individual alkenyl or alkyl succinimides meeting the above requirements and which have in the range of about 14 to about 26 carbon atoms in the alkenyl or alkyl group are preferred. Particularly preferred are individual alkenyl or alkyl succinimide that meet these requirements and have in the range of about 16 to about 22 carbon atoms in the alkenyl or alkyl group.

Mixtures of alkenyl and/or alkyl succinimides as described above wherein the components thereof have in the range of about 12 to about 30 carbon atoms in their respective alkenyl and/or alkyl groups, and that have an average number of carbon atoms in the range of about 14 to about 26 are preferred. More preferred are mixtures of alkenyl and/or alkyl succinimides as described above wherein the components thereof have in the range of about 12 to about 30 carbon atoms in their respective alkenyl and/or alkyl groups, and that have an average number of carbon atoms in the range of about 16 to about 20 are particularly preferred. If desired, the foregoing mixtures can comprise both alkenyl and alkyl succinimide species meeting these requirements. Alternatively, all of the succinimides in the mixture can be either alkenyl succinimides or alkyl succinimides.

The various succinimides and mixtures of succinimides referred to above can be in admixture with relatively small amounts of one or more saturated aliphatic hydrocarbons. The amount of such saturated aliphatic hydrocarbon content, when present, will typically be up to about 5 wt % based on the total weight of the succinimide(s) and the saturated aliphatic hydrocarbon(s) present in the composition.

Particularly preferred are alkenyl succinimides in which the alkenyl group is a $C_{16}$ alkenyl group, or a $C_{18}$ alkenyl group, or a mixture of $C_{16}$ and $C_{18}$ alkenyl groups.

One group of amines that is particularly preferred for use in forming the succinimides of this invention is comprised of one or more alkyl or alkenyl primary monoamines having from about 4 to about 16 carbon atoms in the molecule. Especially preferred succinimides are, therefore, alkenyl succinimides formed from a $C_{16}$ alkenyl succinic anhydride or a $C_{18}$ alkenyl succinic anhydride or a mixture of $C_{16}$ and $C_{18}$ alkenyl succinic anhydrides and one or more alkyl or alkenyl primary monoamines having from about 4 to about 16 carbon atoms in the molecule.

A further embodiment of this invention provides improvements in the sizing of cellulosic pulp in an aqueous medium. In particular, this invention provides in a process of sizing a cellulose fiber in an aqueous paper-making slurry, the improvement which comprises introducing into said slurry as a sizing agent at least one alkenyl and/or alkyl succinimide of this invention. Such a process is often referred to in the art as an internal sizing process.

Still another embodiment of this invention provides improvements in-the external sizing of paper products. More particularly, in a process wherein a sizing agent is applied to the surface of a paper web and is impressed thereon under pressure, this invention provides the improvement wherein the sizing agent comprises at least one alkenyl or alkyl succinimide of this invention. Typically, such sizing agent is applied to either or both sides of the web either in the form of one or more aqueous sprays in which the sizing agent has been suitably emulsified or by use of a size press wherein an aqueous emulsion of the sizing agent is maintained in the flooded nip of the press through which the web is passed.

A feature of this invention is that the succinimides provided pursuant to this invention when properly used are highly effective both in internal sizing operations and in external sizing operations. Typically these sizing operations are conducted in the presence of at least one filler and/or at least one pigment, such as precipitated calcium carbonate, titanium dioxide, clay, or the like.

The particular way in which the succinimide sizing agent is utilized for internal or external sizing is not relevant to this invention, because the succinimide(s) of this invention can be used in virtually any known kind of cellulosic or paper sizing operation. The chief requirement is that a suitable sizing amount of one or more succinimides of this invention is brought into contact with the substrate to be sized and is caused to react therewith. In conducting an internal or external sizing operation, the succinimide(s) of this invention can be used as the sole sizing agent, or such succinimide (s) can be used in combination with other suitable pulp or paper sizing agents, such as an alkenyl succinic anhydride sizing agent or a ketene dimer sizing agent.

Additional embodiments and features of this invention will become still further apparent from the ensuing description and the appended claims.

FURTHER DETAILED DESCRIPTION

Succinic Anhydride Intermediates

Suitable internal olefins for use in preparing the alkenyl succinic anhydride intermediates have been identified above. These internal olefins are typically prepared by the isomerization of alpha-olefins which in turn are usually produced either by ethylene chain growth technology or by thermal cracking of paraffin waxes. Ethylene chain growth processing typically involves use of an aluminum alkyl notably triethyl aluminum, and this results in the preparation of alpha-olefins having even numbers of carbon atoms in the molecule. If ethylene chain growth is conducted starting with tripropyl aluminum it is possible to produce mixtures of odd numbered alpha-olefin components. Processes based on cracking of paraffin waxes typically produce alpha-olefin mixtures of even and odd numbered carbon atoms.

Alpha-olefins formed by chain growth of ethylene using process technology such as described in U.S. Pat. Nos. 3,391,175 and 3,391,219 can be used in forming the succinimides of this invention. Alternatively, such alpha-olefins can be isomerized to form the preferred internal olefins used in forming preferred alkenyl succinimides of this invention.

The best way of isomerizing alpha-olefins to internal olefins involves catalytic photoinitiated isomerization of the alpha-olefins to internal olefins using iron pentacarbonyl as the catalyst. For details concerning such processing, see for example, Fleckner et al., *J. Am. Chem. Soc.*, 1984, 106, 2027–2032; Kane et al., *Polyhedron*, 1985, 4, 533–538; and Darsillo et al., *Inorg. Chem.*, 1988, 27, 2815–2819.

Methods for preparing alkenyl succinic anhydrides from olefins and maleic anhydride are well known and are reported in the literature. Preferably the process used will be a thermal process wherein the ene reaction takes place. If desired, one or more additives can be included in the reaction mixture to inhibit color tar, or polymer formation during the thermal process. See, for example, U.S. Pat. Nos. 4,958,034 and 5,021,169 and references cited therein, for details concerning the thermal process and use of additives therein to inhibit tar and color formation. The use of such additives may not be required, however, especially if the process is performed at a temperature in the range of about 240 to about 250° C. using an excess of olefin, and the reaction is terminated before reaching complete conversion.

There are a few additional points worthy of note concerning the olefins used in the ene reaction. First of all, when preparing a mixture of alkenyl succinic anhydrides, the olefins need not be physically blended together prior to use in forming the intermediate succinic anhydride mixture. The olefins can be fed into the reaction mixture concurrently or sequentially, and either individually or in one or more subcombinations or partial mixtures. However, for best results, the mixture of olefins is either performed in a separate blending operation and then the complete blend is fed into the reactor in which the ene reaction is to be performed, or the olefin components are blended together individually or in one or more subcombinations in the reactor in which the ene reaction is to be performed. However formed or used, the overall combination or mixture of the requisite number and types of olefin components are to be used in the requisite relative proportions to form the desired alkenyl succinic anhydride intermediate.

The blending or feeding of the olefins can be conducted at room temperature when the components and the proportions thereof are such that the resultant blend is a liquid at room temperature. Alternatively, the blending can be conducted at suitable elevated temperatures in order to facilitate the blending or feeding where solid olefin components are being fed into the blending vessel or the ene reactor.

Typically the olefins used in the formation of the intermediate alkenyl succinic anhydride are (a) internal olefins, especially linear internal olefins, or (b) trisubstituted olefins having only one branch which is either a methyl group or a methylene group, or (c) a mixture or combination of (a) and (b). However in the practice of this invention, advantages in viscosity and melting point control can be achieved by utilizing a suitable amount of linear alpha olefins (1-olefins) as starting materials in the formation of the alkenyl succinic anhydride intermediate. Typically, when using mixtures of olefins in forming the alkenyl succinic anhydride intermediates, the olefin raw materials used may contain up to about 30 wt % of linear alpha olefins with the balance being linear internal olefins and/or trisubstituted olefins having only one branch which is either a methyl group or a methylene group. Accordingly, the presence of such amounts of 1-olefins in the overall olefin raw material feedstock is included within the scope of this invention.

It is important to observe that the alkenyl succinic anhydride or mixture of alkenyl succinic anhydrides used as intermediates in the production of the succinimides of this invention is formed from synthetic olefins, and not from polymers such as polyethylene, polypropylene, polybutylene, or polyisobutylene.

Succinimides of this Invention

The essential requirements and characteristics of the succinimides of this invention are satisfied by using in the ene reaction an olefin or olefin mixture described above, and by using a suitable amine in the imidization reaction.

Illustrative internal olefins which can be used in forming the alkenyl succinic anhydride intermediates include, for example, 2-tetradecene, 3-tetradecene, 4-tetradecene, 5-tetradecene, 6-tetradecene, 7-tetradecene, 2-pentadecene, 3-pentadecene, 4-pentadecene, 5-pentadecene, 6-pentadecene, 7-pentadecene, and their higher homologs and straight chain analogs having up to about 30 carbon atoms per molecule, 5-methyl-tridec-4-ene, 5-methyl-tridec-5-ene, 3-methyl-tridec-2-ene, 3-methyl-tridec-3-ene, and their higher homologs and analogs having up to about 30 carbon atoms per molecule. As noted above, individual internal olefins meeting these structural requirements can be employed as raw materials in the synthesis of the alkenyl succinic anhydride intermediates. Alternatively, mixtures of such internal olefins can be employed. Illustrative alpha olefins which can be used in combination with such internal olefins in forming the alkenyl succinic anhydride intermediates include, for example, 1-tetradecene, 1-pentadecene, 1-hexadecene, 1-heptadecene, 1-octadecene, 1-nonadecene, 1-eicosene, and their higher homologs having up to about 30 carbon atoms per molecule. Here again, individual or mixtures of 1-olefins of this type can be used in admixture with one or more of the foregoing types of internal olefins as raw materials in the synthesis of the alkenyl succinic anhydride intermediates.

Aliphatic primary monoamines which can be utilized in forming the succinimides of this invention are exemplified by such compounds as, for example, n-butylamine, n-pentylamine, n-heptylamine, n-octylamine, and their higher homologs having up to about 20 carbon atoms in the molecule, and their olefinically unsaturated analogs such as oleylamine. Illustrative examples of alkylene diamines which can be used in forming the succinimides of this invention include such compounds as ethylene diamine, propylene diamine (1,3-propanediamine), butylene diamine (1,4-butane diamine), 1,5-pentane diamine, hexamethylene diamine (1,6-hexane diamine), and their higher homologs having up to about 14 carbon atoms and preferably up to about 10 carbon atoms per molecule. Alkylene polyamines which can be used in the formation of the succinimides of this invention typically contain from 3 to about 10 and preferably from 3 to about 6 nitrogen atoms per molecule and from 4 to about 18 and preferably 4 to about 10 carbon atoms per molecule. Still other types of aliphatic polyamines can be used in the formation of the succinimides of this invention, such as for example, N,N-diethyl-diethylene triamine, N,N-dimethyl-triethylene tetramine, and analogous compounds. The amines can be used either as individual compounds or as mixtures of compounds in forming the succinimides of this invention.

Sizing Operations

Methods for using sizing agents for sizing paper and related cellulosic products is well known and described in the literature. See, for example, Kirk-Othmer, *Encyclopedia of Chemical Technology*, Third Edition, John Wiley and Sons, New York, copyright 1981, Volume 16, pages 803–825 and applicable references cited therein. Also see U.S. Pat. No. 5,114,538 and references cited therein.

Typically, the sizing agent(s) is utilized in the form an aqueous emulsion. Methods and materials for accomplishing such emulsification are well known and reported in the literature.

Because of the particular structural characteristics and physical properties possessed by the succinimides of this invention, they can be effectively utilized in both internal and in external sizing operations. In both such operations, an advantage of their use is their superior hydrolytic stability.

ILLUSTRATIVE EXAMPLES

Example 1 describes the general procedure used for the synthesis of various alkenyl succinic anhydride intermediates subsequently used in preparing alkenyl succinimides of this invention. The olefins used in preparing such alkenyl succinic anhydrides were obtained from commercial sources. In particular the $C_{14}$ internal olefin was obtained from Chevron Chemical Company whereas all of the other olefins used were obtained from British Petroleum/Amoco Corporation. Example 2 describes the general procedure used in the imidization reaction wherein the alkenyl succinic anhydrides were reacted with various amines to produce alkenyl succinimides of this invention.

Example 1

A nitrogen-dried stainless steel reactor, equipped with a mechanical stirrer, a thermocouple well, and a nitrogen inlet tube, was charged with the selected olefin or mixture of olefins used for producing the particular alkenyl succinic anhydride intermediate to be used for preparing the ultimate succinimide of this invention. Into the reactor were charged maleic anhydride and the olefin or mixture of olefins in proportions of 1.5 to 2 equivalent(s) of the olefin(s) per equivalent of maleic anhydride. The vessel was then bolted to the reactor frame, and the reaction mixture was purged with nitrogen for approximately 15 minutes. Heat was applied to the reaction mixture either by means of an electrical mantle or by means of a circulating hot oil bath and when the temperature reached approximately 50–60° C. stirring was initiated. The stirrer used was a double helical impeller operated at approximately 900 rpm. The reaction was conducted at temperatures in the range of about 220–230° C. for periods in the range of about 2–6 hours. On completion of the reaction, the reaction mixture was quickly discharged through the bottom valve of the reactor into a suitable Erlenmeyer flask under a nitrogen atmosphere. Unreacted olefin and maleic anhydride were stripped from the reaction mixture under reduced pressure. The reaction mixtures were then further purified by distillation under reduced pressure.

Example 2

A 100-mL round bottom flask equipped with a Dean-Stark trap, a condenser and a magnetic stirrer was charged with 30 grams (1 equivalent) of an alkenyl succinic anhydride product formed as in Example 1, 30 mL of xylene, 1–2 drops of concentrated sulfuric acid, and 1 equivalent of the selected amine having one primary amino group in the molecule or the selected amine having two primary amino groups in the molecule. The reaction mixture was then stirred and heated at reflux (approximately 140° C.) with continuous removal of water until the theoretical amount of water was released or until no further formation of water occurred. The progress of the reaction was monitored by infrared spectroscopy. At the end of the reaction as indicated by disappearance of the anhydride band in the IR spectrum, the reaction mixture was cooled to room temperature. Typically, the reaction time was in the range of about 1–2 hours. After cooling, xylene was removed by distillation under reduced pressure. The resulting yellow-brown oils were used without further purification, except in the cases where a $C_4$ primary amine was used. In those cases, the product was subjected to purification by distillation under reduced pressure. NMR and IR analyses of all of the products indicated that the products contained no free unreacted amine or unreacted alkenyl succinic anhydride.

Example 3

The viscosities of the alkenyl succinimides of this invention formed as in Example 2 were determined at 25° C. and at 80° C. using a Brookfield Digital Viscometer, Model LVDVII Plus operated at a selected shear rate. The procedure used is as follows:

1) The small sample adapter is inserted into its housing, and temperature control is established by circulating constant temperature fluid through the housing.
2) The viscometer alignment is checked, and adjusted if necessary. The viscometer is switched on and an automatic strain gauge zeroing is performed.
3) The test sample is added to the small sample adapter.
4) An appropriate spindle and rotation velocity combination is selected so that the strain gauge reading falls between 20% and 100% of full scale. Once the spindle has been chosen, it is placed into the fluid sample and connected to the instrument using a screw assembly. The spindle identification is then entered into the memory of the instrument.
5) The desired rotational velocity is entered and the motor is switched on. At this point the spindle rotates at the desired velocity.
6) The digital display on the instrument provides for direct readout of temperature, shear rate, shear stress, strain gauge reading, and viscosity. Usually after about 1 minute the readings have stabilized. No calculations by the operator are required. When the readings have stabilized the pertinent information is recorded by the operator from the digital display.

Using Newtonian viscosity standards (Cannon Instrument Co., State College, Pennsylvania) it was found that strain gauge readings between 20% and 100% viscosity results deviate from actual values by no more than 2%. The Table, wherein the starting olefin and the starting amine serve to identify the succinimide, summarizes the results obtained in these viscosity determinations, as well as the conditions used in the respective viscosity determinations. The physical state given in the Table is the physical state of the particular succinimide at room temperature. The viscosity values given in the Table are specified in terms of the temperature, and the shear rate in reciprocal seconds. In the Table I-$C_{16-18}$ represents a commercially available mixture of linear internal olefins composed of approximately 4% $C_{14}$, 50% $C_{16}$, 45.5% $C_{18}$, and 0.5% $C_{20}$ olefins that was used as the raw material in forming the succinimide. Similarly I-$C_{14}$ represents a commercially available linear internal tetradecene product that was used as the raw material in forming the succinimide.

TABLE

| Starting Olefin | Starting Amine | Physical State | Viscosity at 25° C./ Shear rate | Viscosity at 80° C./Shear rate |
| --- | --- | --- | --- | --- |
| I-$C_{16-18}$ | n-butylamine | liquid | 130/15.8 | 11.3/15.8 |
| I-$C_{16-18}$ | n-octylamine | liquid | 90.8/15.8 | 11.2/132 |
| I-$C_{16-18}$ | n-dodecylamine | liquid | 165.5/15.8 | 8.31/132 |
| I-$C_{16-18}$ | n-octadecylamine | solid | — | 11.7/132 |
| I-$C_{16-18}$ | diethylene triamine | liquid | 4195/2.04 | 87.4/39.6 |
| I-$C_{14}$ | n-butylamine | liquid (distilled) | 65.9/39.6 | 7.98/132 |
| I-$C_{14}$ | n-octadecylamine | solid | — | 20.0/79.2 |

It will be appreciated that acylating agents corresponding to maleic anhydride can be used in preparing the alkenyl succinic anhydrides used in forming the alkenyl succinimides of this invention. For example, maleic acid, the mono or dimethyl ester thereof, or the acid chlorides thereof can be used in lieu of, or in addition to, maleic anhydride. Because of its excellent reactivity, use of maleic anhydride itself is preferred. It will also be appreciated that essentially equivalent products can be formed by using acylating agents closely related to maleic anhydride such as citraconic anhydride, itaconic anhydride, dimethyl maleic anhydride, and their corresponding acids, lower alkyl esters, or acid halides to form a suitable anhydride for use as the intermediate for the synthesis of a related succinimide.

It is to be understood and appreciated that the foregoing Examples and experimental evaluations are presented for the purposes of illustration. They are not intended to constitute, and should not be construed as constituting, limitations on the scope of this invention.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. An alkenyl and/or alkyl succinimide formed from at least one alkenyl or alkyl succinic anhydride and at least one aliphatic amine having one or two primary amino groups in the molecule, wherein:
   a) each alkenyl or alkyl group of said succinimide contains in the range of about 12 to about 30 carbon atoms, and is bifurcated on its alpha carbon atom into two branches neither of which contains less than 2 carbon atoms, one such branch being free of any side chain, and the other such branch either being free of any side chain or containing at most one methyl or methylene side chain; and
   b) said succinimide has a viscosity at 80° C. of less than about 100 centistokes.

2. An alkenyl and/or alkyl succinimide of claim 1 wherein said succinimide is formed from one alkenyl or alkyl succinic anhydride and one said aliphatic amine.

3. An alkenyl and/or alkyl succinimide of claim 1 wherein said succinimide is formed from at least two different alkenyl or alkyl succinic anhydrides and one said aliphatic amine.

4. An alkenyl and/or alkyl succinimide of claim 1 wherein said succinimide is formed from at least two different aliphatic amines and one said alkenyl or alkyl succinic anhydride.

5. An alkenyl and/or alkyl succinimide of claim 1 wherein said succinimide is formed from at least two different alkenyl or alkyl succinic anhydrides and at least two different aliphatic amines.

6. An alkenyl succinimide in accordance with claim 1 wherein said succinimide is formed from one alkenyl succinic anhydride and one said aliphatic amine.

7. An alkenyl succinimide in accordance with claim 1 wherein said succinimide formed from at least two different alkenyl succinic anhydrides and one said aliphatic amine.

8. An alkenyl succinimide of claim 1 wherein said succinimide is formed from at least two different aliphatic amines and one said alkenyl succinic anhydride.

9. An alkenyl succinimide of claim 1 wherein said succinimide is formed from at least two different alkenyl succinic anhydrides and at least two different aliphatic amines.

10. A succinimide of claim 1 wherein said at least one aliphatic amine is an alkyl or alkenyl primary monoamine.

11. A succinimide of claim 1 wherein said at least one aliphatic amine is an alpha omega alkylene diamine.

12. A succinimide of claim 1 wherein said at least one aliphatic amine is an alkylene polyamine having two terminal primary amino groups and at least one internal secondary amino group.

13. A succinimide of claim 1 wherein said at least one aliphatic amine is an alkylene polyamine having one terminal primary amino group and at least one secondary or tertiary amino group.

14. An alkenyl succinimide of any of claims 6, 7, 8 or 9 wherein said aliphatic amine is an alkyl or alkenyl primary monoamine having up to about 20 carbon atoms in the molecule.

15. An alkenyl succinimide of any of claims 6, 7, 8 or 9 wherein said aliphatic amine is an alpha omega alkylene diamine having up to about 14 carbon atoms in the molecule.

16. An alkenyl succinimide of any of claims 6, 7, 8 or 9 wherein said aliphatic amine is an alkylene polyamine having two terminal primary amino groups and at least one internal secondary amino group having from 3 about 10 nitrogen atoms and from 4 to about 18 carbon atoms in the molecule.

17. A composition comprising at least one alkenyl or alkyl succinimide in which (i) there are from 1 to 2 imidized alkenyl or alkyl succinic moieties per molecule, (ii) the alkenyl or alkyl group of each such moiety contains in the range of about 12 to about 30 carbon atoms, (iii) each such alkenyl or alkyl group is bifurcated on its alpha carbon atom into two branches neither of which contains less than 2 carbon atoms, one such branch being free of any side chain, and the other such branch either being free of any side chain or containing at most one methyl or methylene side chain, (iv) the imidizing moiety of the succinimide has one of the formulas (1) through (5) as follows:

 (1)

 (2)

 (3)

 (4)

 (5)

where $R^1$ is (a) an alkyl group or (b) an olefinically unsaturated aliphatic hydrocarbon group having therein from 1 to 3 olefinic double bonds, said group (a) or (b) having in the range of 2 to about 20 carbon atoms, $R^2$ is a hydrogen atom or an alkyl group, n is an integer in the range of 0 to 5, and $R^2$ has a total number of carbon atoms in the range of 2 to about 15, and $R^3$ is an alkylene group having from 2 to about 10 carbon atoms, and (v) the succinimide has a viscosity at 80° C. of less than about 100 centistokes.

18. In a process of sizing a cellulose fiber in an aqueous paper-making slurry, the improvement which comprises introducing into said slurry as a sizing agent an alkenyl and/or alkyl succinimide formed from at least one alkenyl and/or alkyl succinic anhydride and at least one aliphatic amine having one or two primary amino groups in the molecule, said succinimide being characterized in that:
   a) each alkenyl or alkyl group thereof contains in the range of about 12 to about 30 carbon atoms, and is bifurcated on its alpha carbon atom into two branches neither of which contains less than 2 carbon atoms, one such branch being free of any side chain, and the other such branch either being free of any side chain or containing at most one methyl or methylene side chain; and b) said succinimide has a viscosity at 80° C. of less than about 100 centistokes.

19. The improvement according to claim 18 wherein said sizing agent is an alkenyl succinimide formed from one alkenyl succinic anhydride, and one alkyl or alkenyl primary monoamine having up to about 20 carbon atoms in the molecule.

20. The improvement according to claim 18 wherein said sizing agent is an alkenyl succinimide formed from at least two different alkenyl succinic anhydrides, and one alkyl or alkenyl primary monoamine having up to about 20 carbon atoms in the molecule.

21. The improvement according to claim 18 wherein said sizing agent is an alkenyl succinimide formed from at least two different alkyl or alkenyl primary monoamines each having up to about 20 carbon atoms in the molecule, and one said alkenyl succinic anhydride.

22. The improvement according to claim 18 wherein said sizing agent is an alkenyl succinimide formed from at least two different alkenyl succinic anhydrides, and at least two alkyl or alkenyl primary monoamines each having up to about 20 carbon atoms in the molecule.

23. In a process wherein a sizing agent is applied to the surface of a paper web and is impressed thereon under pressure, the improvement wherein the sizing agent comprises at least one alkenyl and/or alkyl succinimide formed from at least one alkenyl and/or alkyl succinic anhydride and at least one aliphatic amine having one or two primary amino groups in the molecule, said succinimide being characterized in that:

a) each alkenyl or alkyl group thereof contains in the range of about 12 to about 30 carbon atoms, and is bifurcated on its alpha carbon atom into two branches neither of which contains less than 2 carbon atoms, one such branch being free of any side chain, and the other such branch either being free of any side chain or containing at most one methyl or methylene side chain; and b) said succinimide has a viscosity at 80° C. of less than about 100 centistokes.

24. The improvement of claim 23 wherein said sizing agent is applied to one or both sides of said web in the form of one or more sprays of an aqueous emulsion containing the sizing agent.

25. The improvement of claim 23 wherein said sizing agent is applied to both sides of said web by means of a size press having the nip flooded with an aqueous emulsion containing the sizing agent.

26. A composition as in claim 17 wherein said group a) or b) has in the range of 4 to about 18 carbon atoms.

* * * * *